(12) United States Patent
Matsuo et al.

(10) Patent No.: US 11,774,358 B2
(45) Date of Patent: Oct. 3, 2023

(54) GAS ANALYZER

(71) Applicant: YOKOGAWA ELECTRIC CORPORATION, Tokyo (JP)

(72) Inventors: Junichi Matsuo, Musashino (JP); Yusaku Umino, Musashino (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 17/656,576

(22) Filed: Mar. 25, 2022

(65) Prior Publication Data
US 2022/0317040 A1 Oct. 6, 2022

(30) Foreign Application Priority Data

Mar. 30, 2021 (JP) .................. 2021-058447

(51) Int. Cl.
*G01N 21/39* (2006.01)
*G01N 33/00* (2006.01)
(52) U.S. Cl.
CPC ......... *G01N 21/39* (2013.01); *G01N 33/0027* (2013.01); *G01N 2021/399* (2013.01); *G01N 2201/0636* (2013.01); *G01N 2201/06113* (2013.01)
(58) Field of Classification Search
CPC ............... G01N 21/39; G01N 33/0027; G01N 2021/399; G01N 2201/06113; G01N 2201/0636; G01N 2021/0314; G01N 21/85; G01N 2021/8578; G01N 21/01; G01N 2021/0106
See application file for complete search history.

(56) References Cited

U.S. PATENT DOCUMENTS

| | | | |
|---|---|---|---|
| 4,655,548 A * | 4/1987 | Jue | G02B 7/005 359/107 |
| 5,303,035 A | 4/1994 | Luecke et al. | |
| 2014/0211209 A1 | 7/2014 | Ido et al. | |
| 2019/0310188 A1* | 10/2019 | Matsuo | H01S 5/0071 |

FOREIGN PATENT DOCUMENTS

| | | |
|---|---|---|
| CN | 109540800 A * | 3/2019 |
| CN | 109540800 A | 3/2019 |
| JP | S59-226309 | 12/1984 |
| JP | 2000-171736 A | 6/2000 |
| JP | 2002-286969 A | 10/2002 |
| JP | 2019-184368 A | 10/2019 |

\* cited by examiner

*Primary Examiner* — Tarifur R Chowdhury
*Assistant Examiner* — Akbar Hassan Rizvi
(74) *Attorney, Agent, or Firm* — Rankin, Hill & Clark LLP

(57) ABSTRACT

A gas analyzer that easily facilitates alignment is provided. The gas analyzer is a gas analyzer for measuring a predetermined component in a measurement gas by irradiating light on the measurement gas from a light emitting element and receiving light that passes through the measurement gas. The gas analyzer includes a base member configured to be adjustable in position along at least one axis that is not parallel to the optical axis of the light emitting element, and a holding member configured to hold the light emitting element and to be held to the base member in an angularly adjustable manner around at least one axis that is not parallel to the optical axis.

7 Claims, 3 Drawing Sheets

GAS ANALYZER

CROSS-REFERENCE TO RELATED APPLICATION

The present application claims priority to and the benefit of Japanese Patent Application No. 2021-058447 filed Mar. 30, 2021, the entire contents of which are incorporated herein by reference.

TECHNICAL FIELD

The present disclosure relates to a gas analyzer.

BACKGROUND

In a known gas analyzer, such as a laser gas analyzer using Tunable Diode Laser Absorption Spectroscopy (TDLAS), a holding member that holds a light emitting element is adjustable in position along at least one axis that is not parallel to the optical axis of the light emitting element. For example, see patent literature (PTL) 1.

CITATION LIST

Patent Literature

PTL 1: JP 2019-184368 A

SUMMARY

A gas analyzer according to an embodiment is a gas analyzer for measuring a predetermined component in a measurement gas by irradiating light on the measurement gas from a light emitting element and receiving light that passes through the measurement gas, the gas analyzer including a base member configured to be adjustable in position along at least one axis that is not parallel to an optical axis of the light emitting element; and a holding member configured to hold the light emitting element and to be held to the base member in an angularly adjustable manner around at least one axis that is not parallel to the optical axis.

DETAILED DESCRIPTION

Figure 1:
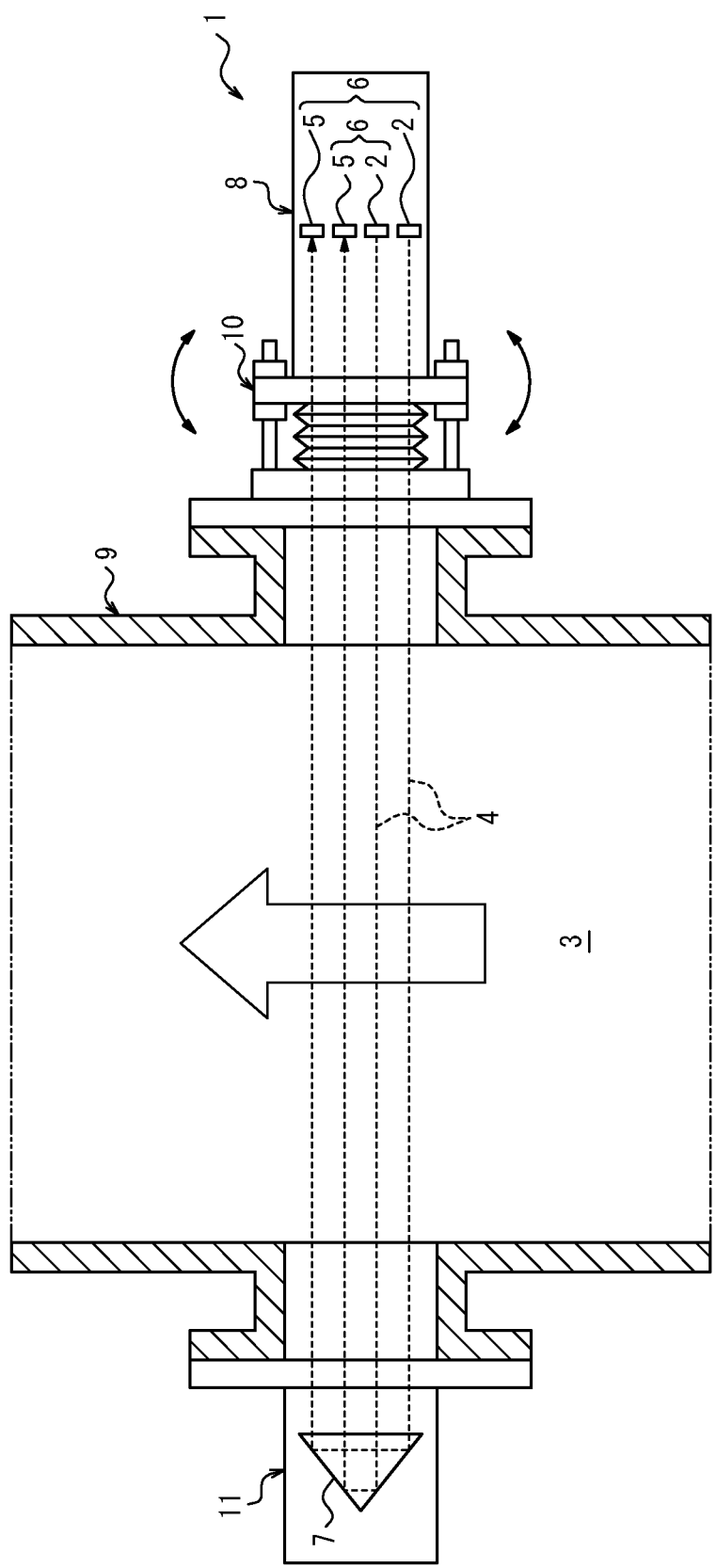
FIG. 1 is a partial cross-sectional side view illustrating a gas analyzer, according to an embodiment, attached to a channel wall.

The aforementioned conventional gas analyzer has room for improvement in terms of easily facilitating the alignment of the position and angle of the optical axis of the light emitting element so that the light irradiated from the light emitting element can be received by a light receiving element.

A gas analyzer according to an embodiment is a gas analyzer for measuring a predetermined component in a measurement gas by irradiating light on the measurement gas from a light emitting element and receiving light that passes through the measurement gas, the gas analyzer including a base member configured to be adjustable in position along at least one axis that is not parallel to an optical axis of the light emitting element; and a holding member configured to hold the light emitting element and to be held to the base member in an angularly adjustable manner around at least one axis that is not parallel to the optical axis. According to this configuration, alignment can easily be facilitated.

A gas analyzer according to an embodiment further includes a plurality of light emitters that each include the base member, the holding member, and the light emitting element. According to this configuration, a plurality of predetermined components in the measurement gas can be measured using the plurality of light emitters. Furthermore, the plurality of light emitters can be aligned independently from each other, thereby achieving easy alignment.

A gas analyzer according to an embodiment further includes a reflector configured to reflect the light irradiated by the light emitting element so that the light travels back and forth in the measurement gas. According to this configuration, the optical path length in the measurement gas can be doubled by the reflector, thereby increasing the measurement accuracy.

In a gas analyzer according to an embodiment, a light emitter and a reflector are separately mounted on a channel wall forming a channel for the measurement gas, the light emitter including the base member, the holding member, and the light emitting element, and the reflector being configured to reflect the light irradiated by the light emitting element so that the light travels back and forth in the measurement gas. According to this configuration, a long optical path length in the measurement gas can be secured, thereby increasing the measurement accuracy.

In a gas analyzer according to an embodiment, the holding member is held to the base member in an angularly adjustable manner around at least two axes that are not parallel to the optical axis. According to this configuration, alignment can more easily be facilitated.

In a gas analyzer according to an embodiment, the base member is adjustable in position along at least two axes that are not parallel to the optical axis. According to this configuration, alignment can more easily be facilitated.

In a gas analyzer according to an embodiment, the gas analyzer uses tunable diode laser absorption spectroscopy. According to this configuration, predetermined components in the measurement gas can be measured accurately.

In a gas analyzer according to an embodiment, the holding member is held to the base member in an angularly adjustable manner around at least one axis that intersects the optical axis. According to this configuration, alignment can more easily be facilitated.

In a gas analyzer according to an embodiment, the holding member is held to the base member in an angularly adjustable manner around at least two axes that each intersect the optical axis and intersect each other. According to this configuration, alignment can more easily be facilitated.

In a gas analyzer according to an embodiment, the base member is adjustable in position along at least one axis that intersects the optical axis. According to this configuration, alignment can more easily be facilitated.

In a gas analyzer according to an embodiment, the base member is adjustable in position along at least two axes that each intersect the optical axis and intersect each other. According to this configuration, alignment can more easily be facilitated.

According to the present disclosure, a gas analyzer that easily facilitates alignment can be provided.

Embodiments of the present disclosure are described below with reference to the drawings.

As illustrated in FIG. 1, a gas analyzer 1 according to the present embodiment uses Tunable Diode Laser Absorption Spectroscopy (TDLAS), for example, to measure a plurality of predetermined components in a measurement gas 3 by irradiating light 4 from a plurality of light emitting elements 2 on the measurement gas 3 and receiving the light 4 that passes through the measurement gas 3.

Tunable Diode Laser Absorption Spectroscopy (TDLAS) is a method of measuring the concentration, for example, of a predetermined component in a measurement gas 3 based on the optical path length in the measurement gas 3 and the intensity difference, i.e., the absorbance, of a specific wavelength component of the light 4 before and after the light 4 passes through the measurement gas 3. Examples of the predetermined component include $CO$, $CO_2$, $H_2O$, $C_nH_m$, $NH_3$, and $O_2$.

In the present embodiment, the gas analyzer 1 includes a plurality of light transmitters/receivers 6, each including a light emitting element 2, such as a laser diode, and a light receiving element 5, such as a photodiode, that receives light 4 irradiated from the light emitting element 2. The gas analyzer 1 also includes a reflector 7 that reflects the light 4 irradiated by the plurality of light emitting elements 2 so that the light 4 travels back and forth in the measurement gas 3. According to the plurality of light transmitters/receivers 6, a plurality of predetermined components in the measurement gas 3 can be measured. The number of light transmitters/receivers 6 is two in the present embodiment, but this example is not limiting, and the number can be increased or decreased as appropriate.

Each light transmitter/receiver 6 is housed in a first housing 8. The first housing 8 is mounted, via an alignment flange 10, on a cylindrical channel wall 9 that forms a channel for the measurement gas 3. The first housing 8 is angularly adjustable with respect to the channel wall 9 by adjustment of the alignment flange 10 (see the bold arrow in FIG. 1). By angular adjustment of the alignment flange 10, the optical axes of the plurality of light emitting elements 2 can be angularly adjusted together.

The reflector 7 is formed by an optical element such as a retro-reflector that reflects the light 4. The reflector 7 is housed in a second housing 11 in an angularly adjustable manner. The second housing 11 is mounted on the channel wall 9 separately from the first housing 8. The optical path length in the measurement gas 3 can be doubled by the reflector 7, thereby increasing the measurement accuracy.

As described above, the gas analyzer 1 according to the present embodiment is an opposing type that includes two mounting portions (the first housing 8 and the second housing 11) that face each other across a channel. The gas analyzer 1 is also a reflecting type that includes the reflector 7 and is a multiple optical axis type that includes the plurality of light emitting elements 2. Opposing types, reflecting types and multiple optical axis types tend to have a higher degree of difficulty in alignment, and the gas analyzer 1 according to the present embodiment, which falls under all of these types, tends to have a particularly high degree of difficulty in alignment.

To address this, the gas analyzer 1 according to the present embodiment is configured so that the positions and angles (directions) of the plurality of optical axes can be adjusted independently of each other to facilitate alignment. More specifically, the gas analyzer 1 includes a plurality of light emitters 14 that each include a base member 12, a holding member 13, and the light emitting element 2. Since the light emitters 14 have similar configurations, one light emitter 14 is illustrated in detail below.

Figure 2A:
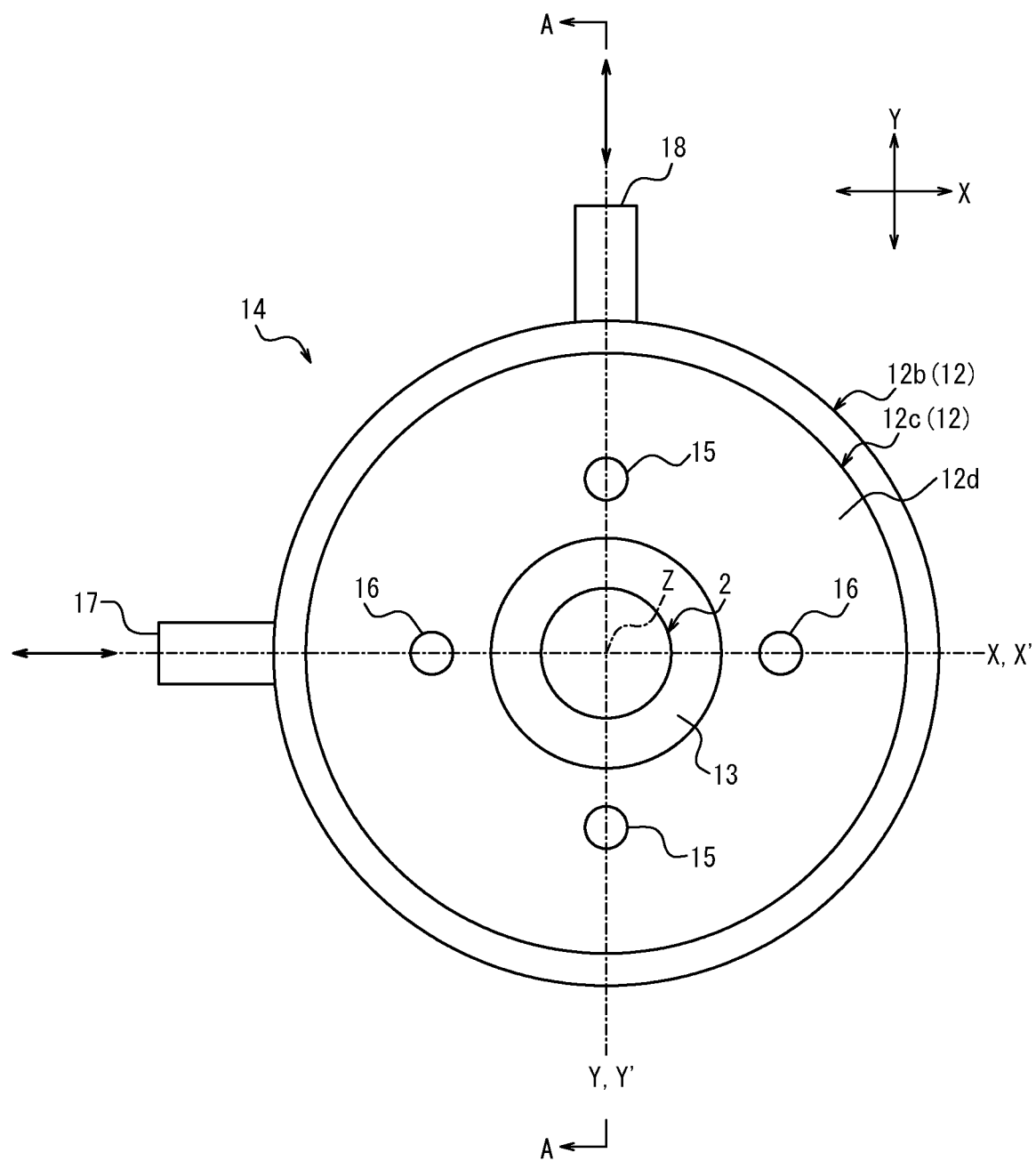
FIG. 2A is a plan view of a light emitter in the gas analyzer illustrated in FIG. 1.
Figure 2B:
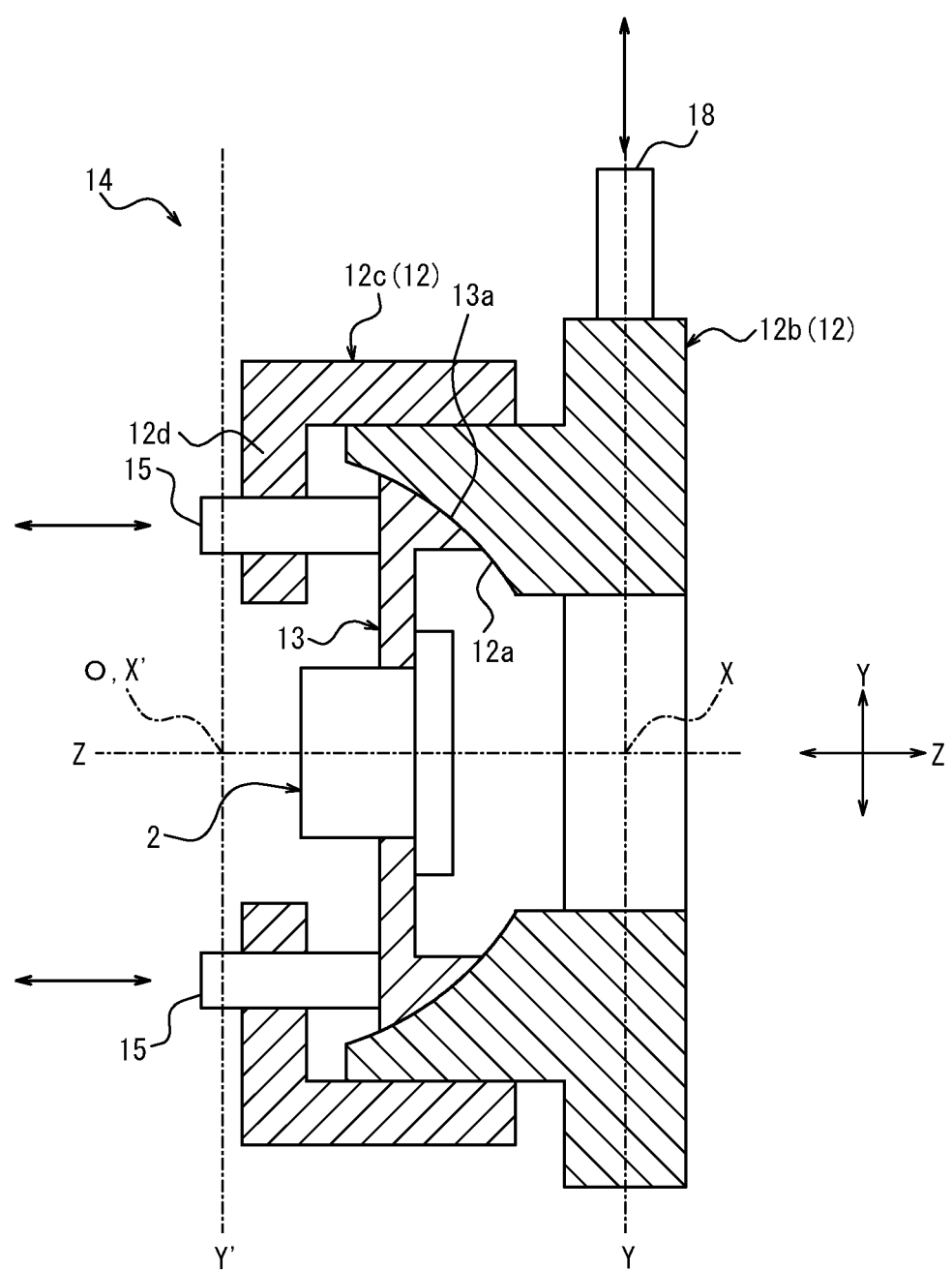
FIG. 2B is a cross-sectional view along the A-A line in FIG. 2A.

As illustrated in FIGS. 2A and 2B, the holding member 13 holds the light emitting element 2. The light emitting element 2 emits light 4 along an optical axis. The axis coinciding with the optical axis is referred to below as the Z-axis. The holding member 13 has an annular shape centered on the Z-axis and integrally holds the light emitting element 2 at the inner circumferential edge of the holding member 13. The holding member 13 has a contact surface 13a that is annular, centered on the Z-axis, and that forms a shape along a spherical surface having a spherical center O on the Z-axis.

The base member 12 has an annular shape centered on the Z-axis when the holding member 13 is in the neutral position illustrated in FIG. 2B. The neutral position refers to a position at which the Z-axis is perpendicular to both the below-described X-direction and the below-described Y-direction. More specifically, the base member 12 includes a receptive member 12b, which has a contacted surface 12a contacted by the contact surface 13a of the holding member 13, and a frame member 12c integrally attached to the receptive member 12b. The contacted surface 12a has an annular shape centered on the Z-axis when the holding member 13 is in the neutral position and forms a shape along a spherical surface that defines the shape of the contact surface 13a. The frame member 12c has an opposing wall 12d that, when the holding member 13 is in the neutral position, faces the contacted surface 12a in the Z-direction along the Z-axis and has an annular shape centered on the Z axis.

Two X'-axis adjustment screws 15, provided along the Y'-axis on opposite sides of the Z-axis as viewed in the Z-direction when the holding member 13 is in the neutral position, are attached to the opposing wall 12d in a manner enabling forward and backward movement in the Z-direction when the holding member 13 is in the neutral position. Here, the X'-axis and Y'-axis each pass through the spherical center O, and when the holding member 13 is in the neutral position, the X'-axis and Y'-axis each intersect the Z-axis at right angles and intersect each other at right angles. The holding member 13 is sandwiched between the tips of the two X'-axis adjustment screws 15 and the contacted surface 12a. Therefore, by adjustment of the Z-direction positions of the two X'-axis adjustment screws 15 (i.e., when one X'-axis adjustment screw 15 is moved backward while the other X'-axis adjustment screw 15 is moved forward), the holding member 13 and the light emitting element 2 held by the holding member 13 are rotated around the X'-axis, thereby adjusting the angle of the optical axis around the X'-axis (adjustment of the inclination angle of the optical axis relative to the optical axis in the neutral position).

Two Y'-axis adjustment screws 16, provided along the X'-axis on opposite sides of the Z-axis as viewed in the Z-direction when the holding member 13 is in the neutral position, are attached to the opposing wall 12d in a manner enabling forward and backward movement in the Z-direction when the holding member 13 is in the neutral position. The holding member 13 is sandwiched between the tips of the two Y'-axis adjustment screws 16 and the contacted surface 12a. Therefore, by adjustment of the Z-direction positions of the two Y'-axis adjustment screws 16 (i.e., when one Y'-axis adjustment screw 16 is moved backward while the other Y'-axis adjustment screw 16 is moved forward), the holding member 13 and the light emitting element 2 held by the holding member 13 are rotated around the Y'-axis, thereby adjusting the angle of the optical axis around the Y'-axis.

Instead of both the contact surface 13a and the contacted surface 12a having shapes along a spherical surface, only one of the contact surface 13a and the contacted surface 12a may have a shape along a spherical surface. Furthermore, in FIG. 2B, the light emitting element 2 is held facing left (to emit the light 4 to the left) by the holding member 13 (i.e., so that the X'-axis adjustment screws 15 and the Y'-axis adjustment screws 16 are on the front side of the light emitting element 2). Alternatively, while maintaining the orientation of the holding member 13 in FIG. 2B, the light emitting element 2 may be faced to the right and held by the holding member 13 (i.e., so that the X'-axis adjustment screws 15 and the Y'-axis adjustment screws 16 are on the back side of the light emitting element 2).

The base member 12 is held by the first housing 8 in a positionally adjustable manner along the X-axis and Y-axis, which are two axes that each intersect the Z-axis at right angles and intersect each other at right angles when the holding member 13 is in the neutral position. For example, the base member 12 is adjustable in position along the X-direction via an X-direction adjustment screw 17 that can move forward and backward in the X-direction along the X-axis and is adjustable in position along the Y-direction via a Y-direction adjustment screw 18 that can move forward and backward in the Y-direction along the Y-axis. The X-axis and X'-axis are parallel to each other, and the Y-axis and Y'-axis are parallel to each other.

In this way, the optical axes can be moved in parallel by adjusting the position of the base member 12, and the optical axes can be inclined by adjusting the angle of the holding member 13.

As described above, the opposing, reflecting, and multiple optical axis type gas analyzer 1 according to the present embodiment includes a plurality of light emitters 14 that can adjust the position and angle of the optical axes independently of each other, thereby achieving easy alignment.

The above embodiment is an example of the present disclosure, and a variety of modifications may be made.

For example, the gas analyzer 1 according to the above embodiment can be modified in various ways, as described below.

Various modifications can be made to the gas analyzer 1 according to the above embodiment, as long as the gas analyzer 1 is for measuring a predetermined component in the measurement gas 3 by irradiating light 4 on the measurement gas 3 from the light emitting element 2 and receiving the light 4 transmitted through the measurement gas 3, and as long as the gas analyzer 1 includes the base member 12 configured to be adjustable in position along at least one axis that is not parallel to the optical axis of the light emitting element 2, and the holding member 13 configured to hold the light emitting element 2 and to be held to the base member 12 in an angularly adjustable manner around at least one axis that is not parallel to the optical axis.

For example, the gas analyzer 1 according to the above embodiment includes two light emitting elements 2, but this configuration is not limiting. The gas analyzer 1 may include one light emitting element 2 or may include three or more light emitting elements 2.

In the gas analyzer 1 according to the above embodiment, the base member 12 is adjustable in position along two axes (the X-axis and Y-axis), but the base member 12 may be adjustable in position along one axis, or the base member 12 may be adjustable in position along three or more axes. In the gas analyzer 1 according to the above embodiment, the X-axis and the Y-axis are orthogonal, but this configuration is not limiting. The X-axis and the Y-axis may intersect at an angle other than a right angle.

In the gas analyzer 1 according to the above embodiment, the holding member 13 is adjustable in angle around two axes (the X'-axis and Y'-axis), but this configuration is not limiting. The holding member 13 may be adjustable in angle around one axis or may be adjustable in angle around three or more axes. In the gas analyzer 1 according to the above embodiment, the X'-axis and the Y'-axis are orthogonal, but this configuration is not limiting. The X'-axis and the Y'-axis may intersect at an angle other than a right angle. In the gas analyzer 1 according to the above embodiment, the X-axis and the X'-axis are parallel to each other, but this configuration is not limiting. In the gas analyzer 1 according to the above embodiment, the Y-axis and the Y'-axis are parallel to each other, but this configuration is not limiting.

The gas analyzer 1 according to the above embodiment is a reflecting type that includes the reflector 7, but this configuration is not limiting. The gas analyzer 1 may be a non-reflecting, opposing type in which the light emitting element 2 and the light receiving element 5 are mounted facing each other across a channel. The gas analyzer 1 according to the above embodiment is an opposing type, but this configuration is not limiting. The gas analyzer 1 may be a probe type in which only one part is attached to the channel wall 9, with the reflector 7 being arranged in the channel.

The gas analyzer 1 according to the above embodiment is preferably a gas analyzer 1 including a plurality of light emitters 14 that each include the base member 12, the holding member 13, and the light emitting element 2.

The gas analyzer 1 according to the above embodiment is preferably a gas analyzer 1 including the reflector 7 that reflects the light 4 irradiated by the light emitting element 2 so that the light 4 travels back and forth in the measurement gas 3.

The gas analyzer 1 according to the above embodiment is preferably a gas analyzer 1 in which the light emitter 14 and the reflector 7 are separately mounted on the channel wall 9 forming the channel for the measurement gas 3, the light emitter 14 including the base member 12, the holding member 13, and the light emitting element 2, and the reflector 7 being configured to reflect the light 4 irradiated by the light emitting element 2 so that the light 4 travels back and forth in the measurement gas 3.

The gas analyzer 1 according to the above embodiment is preferably a gas analyzer 1 in which the holding member 13 is held to the base member 12 in an angularly adjustable manner around at least two axes that are not parallel to the optical axis.

The gas analyzer 1 according to the above embodiment is preferably a gas analyzer 1 in which the base member 12 is adjustable in position along at least two axes that are not parallel to the optical axis.

The gas analyzer 1 according to the above embodiment is preferably a gas analyzer 1 that uses TDLAS.

The gas analyzer 1 according to the above embodiment is preferably a gas analyzer 1 in which the holding member 13 is held to the base member 12 in an angularly adjustable manner around at least one axis that intersects the optical axis.

The gas analyzer 1 according to the above embodiment is preferably a gas analyzer 1 in which the holding member 13 is held to the base member 12 in an angularly adjustable manner around two axes that each intersect the optical axis and that intersect each other.

The gas analyzer 1 according to the above embodiment is preferably a gas analyzer 1 in which the base member 12 is adjustable in position along at least one axis that intersects the optical axis.

The gas analyzer 1 according to the above embodiment is preferably a gas analyzer 1 in which the base member 12 is adjustable in position along two axes that each intersect the optical axis and that intersect each other.

The invention claimed is:

1. A gas analyzer for measuring a predetermined component in a measurement gas by irradiating light on the measurement gas from a light emitting element and receiving light that passes through the measurement gas, the gas analyzer comprising:
   a housing;
   a base member configured to be held by the housing in a positionally adjustable manner along at least one axis that is not parallel to an optical axis of the light emitting element; and
   a holding member configured to hold the light emitting element and to be held to the base member in an angularly adjustable manner around at least one axis that is not parallel to the optical axis,
   wherein the holding member has a contact surface,
   wherein the base member includes a receptive member, which has a contacted surface contacted by the contact surface of the holding member, and a frame member integrally attached to the receptive member,
   wherein at least one of the contact surface and the contacted surface forms a shape along a spherical surface,
   wherein the frame member has an opposing wall,
   wherein two adjustment screws, which can angularly adjust the holding member, are attached to the opposing wall in a manner enabling forward and backward movement, and the holding member is sandwiched between tips of the two adjustment screws and the contacted surface.

2. The gas analyzer of claim 1, further comprising a plurality of light emitters that each include the base member, the holding member, and the light emitting element.

3. The gas analyzer of claim 1, further comprising a reflector configured to reflect the light irradiated by the light emitting element so that the light travels back and forth in the measurement gas.

4. The gas analyzer of claim 1, wherein a light emitter and a reflector are separately mounted on a channel wall forming a channel for the measurement gas, the light emitter comprising the base member, the holding member, and the light emitting element, and the reflector being configured to reflect the light irradiated by the light emitting element so that the light travels back and forth in the measurement gas.

5. The gas analyzer of claim 1, wherein the holding member is held to the base member in an angularly adjustable manner around at least two axes that are not parallel to the optical axis.

6. The gas analyzer of claim 1, wherein the base member is adjustable in position along at least two axes that are not parallel to the optical axis.

7. The gas analyzer of claim 1, wherein the gas analyzer uses tunable diode laser absorption spectroscopy.

* * * * *